Jan. 14, 1964 E. G. FISHER Plant Pat. 2,342
ROSE PLANT
Filed Feb. 1, 1963
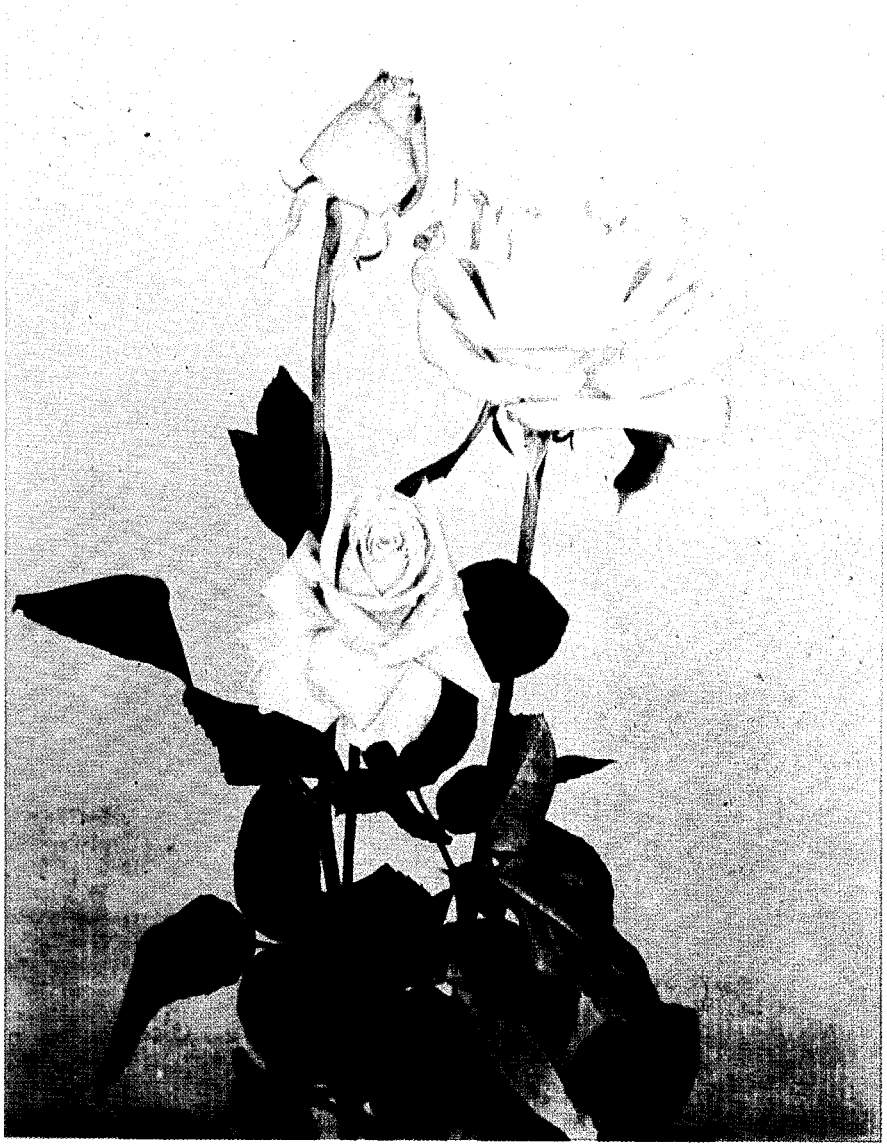
Esther Gladys Fisher
By
Burns, Doane, Benedict, Anderson & Mathis
Attorneys.

United States Patent Office

Plant Pat. 2,342

Patented Jan. 14, 1964

2,342

ROSE PLANT

Esther Gladys Fisher, Woburn, Mass., assignor to Arnold-Fisher Company, Woburn, Mass., a corporation of Massachusetts Filed Feb. 1, 1963, Ser. No. 255,708
1 Claim. (Cl. Plt.—18)

The present invention relates to a new and distinct variety of rose plant of the hybrid tea class, which was originated by me by crossing the rose "Peace" (Plant Patent No. 591) and an unpatented and unnamed pink rose seedling formely bred by me.

The primary objective of this breeding was to produce a new rose variety in which there is combined the best characteristics of the parent varieties, and more particularly, which is useful for growing in the greenhouse for the florist trade.

In achieving this objective, in making the cross aforementioned, I used as female parent the rose named "Peace" which has not only a flower of great size and beauty, but also a stem and neck of great strength and vigor. The male parent chosen was characterized by having a long, fairly strong stem but with a neck of insufficient strength to sustain the bloom when open. The resulting seedling of these parents achieved the following unique combination of characteristics which not only distinguish the same from the parents, but also from all other varieties of which I am aware:

(1) Long and strong flower stems and a strong neck, thereby making the new variety especially suitable for cut flowers which are usually priced according to the length of the stems;

(2) A habit of blooming as well in the winter as in the summer, thus making possible the sale of this rose throughout every day of the year.

(3) Flower buds of fairly long and high-centered form, especially suitable for the florist trade.

(4) The large number of petals which makes the rose desirable for shipping and keeping in the florist shops, since any outer petals that may become bruised can be removed, still leaving a large double flower to be sold.

(5) A distinctly different shade of pink which gives variety to the shades now available to the public.

Asexual reproduction of my new variety by both grafting and budding, as performed by me in both the green house and out of doors at Woburn, Massachusetts, shows that the aforementioned characteristics and distinctions come true to form and are established and transmitted through succeeding propagations.

The accompanying drawing shows typical specimens of the flowers and foliage of my new variety in different stages of development and as depicted in color as nearly true as it is reasonably possible to make the same in a color illustration of this character.

The following is a detailed description of my new variety with color terminology in accordance with the Nickerson Color Fan, as distributed by the American Horticultural Council, published by Munsell Color Co. (hereinafter abbreviated as "Nickerson") as indicated, except where general color terms of ordinary dictionary significance are obvious:

(Observations made from specimens grown at Woburn, Massachusetts, with the bud and open flower specimens being observed in a greenhouse during the month of November, 1962.)

Type: Greenhouse and outdoor, for cut flowers and for garden decoration.

Class: Hybrid tea.

Breeding: Seedling.

*Seed parent.*—An unnamed pink seedling.

*Pollen parent.*—Peace.

Propagation: Holds its distinguishing characteristics through succeeding propagations by both budding and grafting.

*Plant*

Growth habit: Strong and fast grower; can attain height of 10 to 12 feet but is usually cut back to 7 or 8 feet in the greenhouse; although primarily a greenhouse rose, it grows well out of doors.

Blooming habit: Blooms freely throughout the year in the greenhouse.

Stem: Long (from 18 to 40 inches); very strong.

Color: Moderate olive green 2.5GY 4–3 (Nickerson).

Neck: Very strong; length average 6 inches with tiny beige colored thorns. Color—strong yellow green 5GY 6–8 (Nickerson).

Thorns: Moderate number; varies from 10 to 30 on stems 2 feet in length; largest thorns measure about ¼" in length; slant downward. Color—light olive 7.5Y 5–5 (Nickerson). Tips sometimes have faintest suggestion of reddish cast.

Foliage:

*Type.*—Pinnately compound of 3 to 7 leaflets. Normally five but a surprisingly large number of 7 leaflets (more than is usual in the hybrid tea class).

*Color.*—Upper surface—greyish olive green 5GY 3–2 (Nickerson). Under surface—moderate olive green 5GY 4–3 (Nickerson) overlaid with grayish cast and superimposed over all in a rose red shading.

*Quantity.*—Very abundant.

*Size.*—Large—broad; terminal leaflets average approximately 3½" long by 2⅛" wide.

*Shape.*—long and pointed. From accentuated tip leaf goes from 1" (¾" down from tip) to wide part 2⅛" to 1¼" (¼" from base). Leaflets have acuminate apex with edges serrated with evenly spaced tips (about ⅛" between tips).

*Texture.*—Leathery and firm; semi-glossy or with a glazed polish (not glossy and not dull).

*Leaflet veins.*—Upper surface—well defined, making a definite pattern on the leaf; center vein well defined; reddish tone not very noticeable on veins Under surface—branching veins still noticeable but not as much as on upper surface. However, center vein is more noticeable and color is something like moderate purplish red 5RP 5–10 (Nickerson) overlaying the green.

*Leaflet stem.*—Grooved. Upper surface—moderate olive 7.5Y 4–3 (Nickerson). Under surface same as above only with slight overlay of moderate purplish red 5RP 5–10 (Nickerson).

*Stipules.*—¾" long (to very tips); ⅜" wide when joining stem with well defined points on each side of stem. Color — moderate olive green 2.5GY 4–3 (Nickerson). Base—moderate yellow green 2.5GY 5–5 (Nickerson).

*Flower*

Bud:

*Size.*—Large, 1½ inches long.

*Form.*—Ovid—medium long and high centered.

*Color.*—Varies according to climate and soil condition during year. In our greenhouse on November 29, 1962, was following color. Inside petal: overall effect—purplish pink 7.5RP 7–10 (Nickerson); center part—strong pink 2.5R 7–8 (Nickerson); lower part—light purplish pink 7.5RP 8–5 (Nickerson); base—vivid greenish yellow 7.5Y 8–12; just above base—light yellowish pink 2.5YR 9–3 (Nickerson). Outside petal: varies from strong purplish pink 7.5RP 7–10 (Nickerson) to light purplish pink 7.5RP 8–5 (Nickerson); outer edge—varies from deep pink 2.5R 6–11 to strong pink 2.5R 7–8; base—brilliant greenish yellow 7.5Y 9–8 (Nickerson).

*Sepals.*—Varies from 1″ to the foliaceous type, sometimes as long as 3″. Average length 1¾″ to 2″ width approximately ⅜″ wide at bud. Color: base—strong yellow green 2.5GY 6–8 (Nickerson) blending into moderate yellow green 2.5GY 5–5 (Nickerson); tip—sometimes tinged with dark rose red.

*Calyx (ovary).*—Medium and smooth, approximately ¼″ where joining stem to ⅝″ diameter at top of ovary; is ½″ from top to bottom. Color—moderate yellow green 5GY 5–6 (Nickerson).

*Peduncle.*—Very strong with tiny thorns of beige color—varies, but average from top of ovary to 1st 3 leaflet is 6″; measures ⅜″ thick. Color—strong yellow green 5GY 6–8 (Nickerson).

Bloom:

*Borne.*—Singly on long strong stems, sometimes as long as 3 feet.

*Size when fully open.*—From 5″ to 6″ across.

*Form.*—High centered, opens to a wide-spreading flower which seldom exposes stamens.

*Petalage.*—Average from 50 to 55 petals.

*Scent.*—Delicate and pleasing fragrance.

*Longevity.*—Very long lasting.

Petals:

*Texture.*—Moderately heavy; smooth and suede finish.

*Shape.*—Pear shape; outer petals approximately 2″ to 2¼″ across at widest part to 2½″ from top to bottom. When reflexing, petal takes shape with decided point at top center with a lesser curved point on either side measuring from center point about 1″ to 1½″ down side of petal.

*Color.*—Inside of petal: light purplish pink 5RP 8–5 (Nickerson) lower part to strong purplish pink 5RP 7–9 (Nickerson); effect is a lighter pink for open bloom as compared with bud; base—brilliant greenish yellow 7.5Y 9–8 (Nickerson). Outside of petal: from pale yellow base to lighter yellow which blends to cream white; upper half of petal blending from light purplish pink 7.5RP 8–5 to outer fringe of strong purplish pink 7.5RP 7–10.

Reproductive organs:

*Stamens.*—Fairly short uneven beige yellow filaments with longish shaped pollen tips color moderate orange yellow 1.0YR 8–10 (Nickerson). Uneven lengths but approximately ⅜″ filament to point where pollen sac begins. Pollen sacs fairly abundant.

*Pistil color.*—Red styles tipped with moderate orange yellow 10YR 8–10 (Nickerson). Abundant, of rather uneven length.

Foundation, holding stamens and pistil is fairly large and white; measures ⅛″ to ¼″ high.

I claim:

A new and distinct variety of rose plant of the hybrid tea class, substantially as herein shown and described, characterized particularly as to novelty by the unusually long, strong stem and neck, the large and abundant foliage and the unusual size and beauty of the bloom, the exceptionally large number of petals and a distinctive shade of pink.

No references cited.